United States Patent
Baroni et al.

(10) Patent No.: US 6,936,621 B2
(45) Date of Patent: Aug. 30, 2005

(54) USE OF BENZOYLALKYL-1,2,3,6-TETRAHYDROPYRIDINES

(75) Inventors: Marco Baroni, Vanzago (IT); Rosanna Cardamone, Como (IT); Jacqueline Fournier, Plaisance de Touch (FR); Umberto Guzzi, Milan (IT); Alessandra Ielmini, Arsago Seprio (IT)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 10/729,313

(22) Filed: Dec. 5, 2003

(65) Prior Publication Data

US 2004/0122032 A1 Jun. 24, 2004

Related U.S. Application Data

(60) Continuation of application No. 10/044,221, filed on Nov. 20, 2001, now abandoned, which is a division of application No. 09/331,524, filed on Aug. 5, 1999, now Pat. No. 6,358,965.

(30) Foreign Application Priority Data

Dec. 24, 1996 (FR) .............................. 96 15957

(51) Int. Cl.⁷ .................... A61K 31/435; C07D 211/68
(52) U.S. Cl. ........................ 514/277; 546/340
(58) Field of Search .......................... 546/340; 514/277

(56) References Cited

U.S. PATENT DOCUMENTS

| 5,229,389 A | 7/1993 | Coude et al. |
| 5,270,320 A | 12/1993 | Coude et al. |
| 5,512,584 A | 4/1996 | Steiner et al. |

FOREIGN PATENT DOCUMENTS

WO 91/08200 * 6/1991

OTHER PUBLICATIONS

Schuster et al., Journal of Medicinal Chemistry, vol. 36, No. 24, pp. 3923–3929, (1993).

* cited by examiner

*Primary Examiner*—Patricia L. Morris
(74) *Attorney, Agent, or Firm*—Balaram Gupta

(57) ABSTRACT

The invention relates to the use of compounds of formula

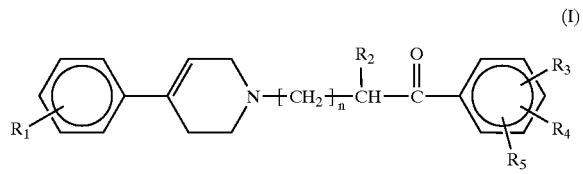

(I)

for the preparation of medicines designed for the treatment of neuronal and cerebral disorders.

The invention also relates to the compounds of formula:

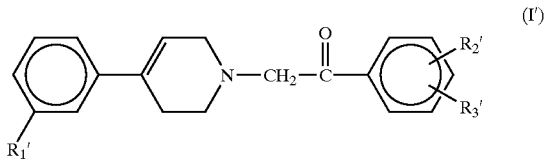

(I')

a process for their preparation and the pharmaceutical compositions containing them.

4 Claims, No Drawings

USE OF BENZOYLALKYL-1,2,3,6-TETRAHYDROPYRIDINES

CROSS REFERENCE TO RELATED APPLICATION

This application is a continuation of application Ser. No. 10/044,221, filed Nov. 20, 2001, (abandoned), which is a divisional of application Ser. No. 09/331,524 filed Aug. 5, 1999, now U.S. Pat. No. 6,358,965.

The present invention relates to the use of certain benzoyl-1,2,3,6-tetrahydropyridines as neurotrophic and neuroprotective agents as well as of novel derivatives, a process for their preparation and pharmaceutical compositions containing them.

EP-0 458 696 describes the use of a 1-(2-naphthylethyl)-4-(3-trifluoromethylphenyl)-1,2,3,6-tetrahydropyridine for the preparation of medicines designed for the treatment of cerebral and neuronal disorders.

WO 91/08200 describes derivatives of tetrahydropyridine with protective activity towards damage caused by hypoxic/ischemic states.

WO 93/11107 describes certain ketones used as intermediates in the preparation of the corresponding alcohols.

It has now been found that certain benzoyl-1,2,3,6-tetrahydropyridines exert a neutrotrophic action on the nervous system similar to that of the nerve growth factor (NGF) and may restore the function of the damaged cells or cells exhibiting anomalies in their physiological functions.

Hence, according to one of its features, the present invention relates to the use of compounds of formula (I)

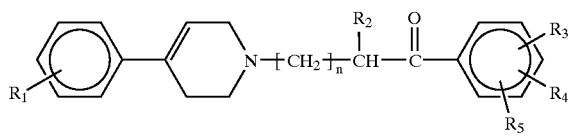

in which
R$_1$ is halogen, a CF$_3$, (C$_1$–C$_4$) alkyl or (C$_1$–C$_4$) alkoxy group;
n is 0 or 1
R$_2$ is hydrogen or a (C$_1$–C$_4$) alkyl group;
R$_3$ is hydrogen, (C$_1$–C$_6$) alkyl, (C$_1$–C$_6$) alkoxy; halogen; a CF$_3$ group, hydroxy, a group selected from (C$_3$–C$_7$) cycloalkyl, phenyl, phenoxy, phenylmethyl or phenylethyl, said group being optionally mono- or polysubstituted on the phenyl group by halogen, CF$_3$, (C$_1$–C$_4$) alkyl or (C$_1$–C$_4$) alkoxy;
R$_4$ and R$_5$ is each independently hydrogen, (C$_1$–C$_6$) alkyl, (C$_1$–C$_6$) alkoxy, halogen, a CF$_3$ group or hydroxy;
as well as to their salts and solvates and their quaternary ammonium salts, for the preparation of medicines designed for the treatment and/or the prophylaxis of the diseases which involve neuronal degeneration.

In the present description the term "(C$_1$–C$_4$) alkyl" designates the groups methyl, ethyl, n-propyl, i-propyl, n-butyl, i-butyl, s-butyl and t-butyl.

The term "(C$_1$–C$_6$) alkyl" designates a hydrocarbon radical containing from 1 to 6 carbon atoms such as, for example, methyl, ethyl, n-propyl, i-propyl, n-butyl, i-butyl, s-butyl, t-butyl, n-pentyl, neopentyl, t-pentyl, n-hexyl, i-hexyl.

When R$_3$ is a phenyl group, the nomenclature given to the biphenyl radical is that in conformity with the IUPAC rules, namely the numbering of the positions of the two rings is the following:

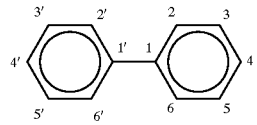

and the radicals having this structure are named:

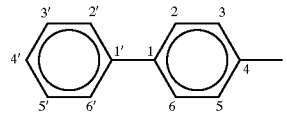

biphenyl-4-yl-

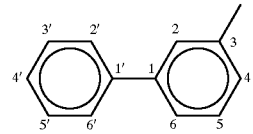

biphenyl-3-yl-

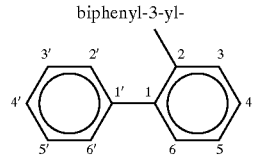

biphenyl-2-yl-

Among the compounds of formula (I), a preferred group is constituted by the compounds of formula (I) where n is zero.

Another preferred group is constituted by the compounds of formula (I) where R$_2$ is hydrogen.

Another preferred group is constituted by the compounds of formula (I) where one of R$_3$, R$_4$ and R$_5$ is hydrogen.

Particularly advantageous compounds according to the present invention are the compounds of formula (I) where the group R$_1$ is a CF$_3$ group in position 3 of the phenyl group.

Among the compounds of formula (I) those of formula (I')

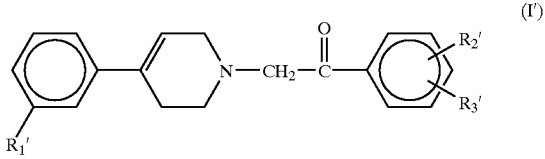

in which
R'$_1$ is halogen, a CF$_3$, (C$_1$–C$_4$) alkyl or (C$_1$–C$_4$) alkoxy group;
R'$_2$ is (C$_1$–C$_6$) alkyl, (C$_1$–C$_6$) alkoxy; halogen, a CF$_3$ group, hydroxy, a group selected from (C$_3$–C$_7$) cycloalkyl, phenyl, phenoxy, phenylmethyl or phenylethyl, said group being optionally mono- or polysubstituted on the phenyl group by halogen, CF$_3$, (C$_1$–C$_4$) alkyl or (C$_1$–C$_4$) alkoxy;
R'$_3$ is hydrogen, (C$_1$–C$_6$) alkyl, (C$_1$–C$_6$) alkoxy, halogen, a CF$_3$ or hydroxy group;
as well as their salts and solvates and their quaternary ammonium salts, are novel compounds and constitute a further feature of the present invention.

The preferred quaternary ammonium salts are those of formula (I″)

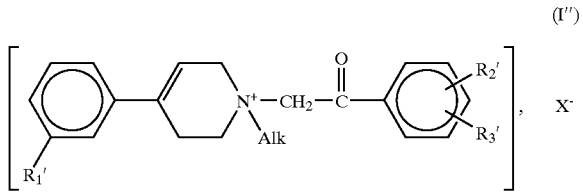

where X⁻ is a pharmaceutically acceptable anion, preferably Cl⁻, Br⁻, I⁻, $CH_3SO_3^-$, $C_6H_5SO_3^-$ and Alk being ($C_1$–$C_4$) alkyl, preferably methyl.

Among the compounds of formula (I′), particularly advantageous compounds are the following:

1-{2-(3′-chlorobiphenyl-4-yl)-2-oxoethyl}-4-(3-trifluoromethyl-phenyl)-1,2,3,6-tetrahydropyridine;
1-{2-(2′-chlorobiphenyl-4-yl)-2-oxoethyl}-4-(3-trifluoromethyl-phenyl)-1,2,3,6-tetrahydropyridine;
1-{2-(4′-chlorobiphenyl-4-yl)-2-oxoethyl}-4-(3-trifluoromethyl-phenyl)-1,2,3,6-tetrahydropyridine;
1-{2-(4-isobutylphenyl)-2-oxoethyl}-4-(3-trifluoromethyl-phenyl)-1,2,3,6-tetrahydropyridine;
1-{2-(4-benzylphenyl)-2-oxoethyl}-4-(3-trifluoromethyl-phenyl)-1,2,3,6-tetrahydropyridine;
1-{2-(4-cyclohexylphenyl)-2-oxoethyl}-4-(3-trifluoromethyl-phenyl)-1,2,3,6-tetrahydropyridine;
1-{2-(4′-fluorobiphenyl-4-yl)-2-oxoethyl}-4-(3-trifluoromethyl-phenyl)-1,2,3,6-tetrahydropyridine;
1-{2-(4-n-butylphenyl)-2-oxoethyl}-4-(3-trifluoromethyl-phenyl)-1,2,3,6-tetrahydropyridine;
1-{2-(biphenyl-4-yl)-2-oxoethyl}-4-(3-trifluoromethyl-phenyl)-1,2,3,6-tetrahydropyridine;
1-{2-(4-t-butylphenyl)-2-oxoethyl}-4-(3-trifluoromethyl-phenyl)-1,2,3,6-tetrahydropyridine;
1-{2-(3,4-diethylphenyl)-2-oxoethyl}-4-(3-trifluoromethyl-phenyl)-1,2,3,6-tetrahydropyridine;
1-{2-(2′-trifluoromethylbiphenyl-4-yl)-2-oxoethyl}-4-(3-trifluoromethyl-phenyl)-1,2,3,6-tetrahydropyridine;
1-{2-(3′-trifluoromethylbiphenyl-4-yl)-2-oxoethyl}-4-(3-trifluoromethyl-phenyl)-1,2,3,6-tetrahydropyridine;
1-{2-(4′-trifluoromethylbiphenyl-4-yl)-2-oxoethyl}-4-(3-trifluoromethyl-phenyl)-1,2,3,6-tetrahydropyridine;

as well as their salts and solvates.

The compounds of formula (I) are prepared as described in WO 91/08200 and WO 93/11107.

According to another of its features, the present invention relates to a process for the preparation of the compounds of formula (I′), their salts or solvates and their quaternary ammonium salts, characterized in that (a) an aryl-1,2,3,6-tetrahydropyridine of formula (II)

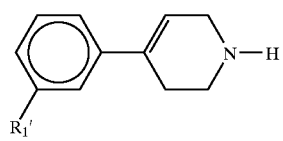

in which R′₁ is as defined above, is reacted with a compound of formula (III)

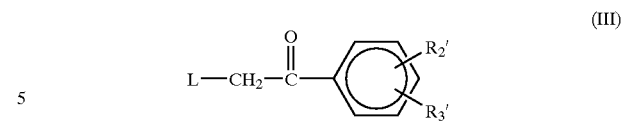

in which R′₂ and R′₃ are as previously defined and L is a leaving group such as, for example, a chlorine, bromine or iodine atom or a methanesulfonyloxy, benzenesulfonyloxy, p-toluenesulfonyloxy, trifluoromethylsulfonyloxy group, bromine being preferred; and (b) the compound of formula (I′) thus obtained is isolated and optionally converted into one of its salts or solvates or one of its quaternary ammonium salts.

The reaction is carried out in an organic solvent at a temperature included between room temperature and the reflux temperature of the solvent used.

An aliphatic alcohol having from 1 to 6 carbon atoms such as methanol, ethanol, isopropanol, n-butanol, n-pentanol is used as preferred organic solvent, but other solvents such as hexane, dimethylformamide, dimethylsulfoxide, sulfolane, acetonitrile, pyridine and the like may also be used.

The reaction is advantageously carried out in the presence of a basic agent such as an alkali hydroxide or carbonate or triethylamine, particularly in the case where L is a halogen atom.

The reaction temperature may vary between room temperature (about 20° C.) and that of reflux and the reaction times vary accordingly. In general, the reaction is terminated after 0.5 to 12 hours of heating at reflux and the final product thus obtained can be isolated according to conventional procedures in the form of the free base or one of its salts or solvates and the free base is optionally converted into one of its salts by simple salification in an organic solvent such as an alcohol, preferably ethanol or isopropanol, an ether like 1,2-dimethoxyethane, ethyl acetate, acetone or a hydrocarbon like hexane.

The compound of formula (I′) obtained and isolated according to the usual procedures is optionally converted into one of its quaternary ammonium salts by reaction with an alkyl halide of formula (IV)

Alk-Hal                                      (IV)

where Alk is ($C_1$–$C_4$) alkyl and Hal is chlorine, bromine or iodine.

The quaternary ammonium salt of formula (I″a) thus obtained

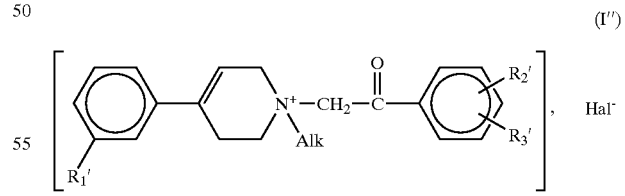

can be converted into another salt for example by an (X⁻) charged anion exchange resin, where X– is a pharmaceutically acceptable anion other than Hal, and preferably the $CH_3SO_3^-$, $C_6H_5SO_3^-$ or p-$CH_3$—$C_6H_5SO_3^-$ (paratoluenesulfonyloxy) anion.

When the salts of the compounds of formula (I) and (I′) are prepared to be administered as medicines, the acids used must be pharmaceutically acceptable; if the salts of the compounds of formula (I) and (I′) are prepared for another purpose, for example to improve the purity or facilitate analytical tests or to separate the enantiomers in the presence of a chiral carbon atom, then any suitable acid or base may be used.

The salts with pharmaceutically acceptable acids are, for example, those with mineral acids such as hydrochloride, hydrobromide, borate, phosphate, sulfate, hydrogen sulfate, hydrogen phosphate or dihydrogen phosphate and those with organic acids such as citrate, benzoate, ascorbate, methylsulfate, naphthalene-2-sulfonate, picrate, fumarate, maleate, malonate, oxalate, succinate, acetate, tartrate, mesylate, tosylate, isethionate, a-ketoglutarate, a-glycerophosphate or glucose-1-phosphate.

The starting amines of formula (II) are known compounds or they can be prepared according to processes similar to those used to prepare the known compounds.

The compounds of formula (III) can be prepared by reaction of the appropriate benzene of formula (V)

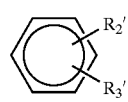

(V)

in which $R'_2$ and $R'_3$ are as previously defined, with an acyl halide of formula L-CH$_2$—CO-Hal in which L and Hal are as previously defined, in the presence of a Lewis acid according to the well-known Friedel-Crafts reaction.

Alternatively, the starting materials (III) where $R'_2$ is an optionally substituted phenyl group may also be prepared by carrying out the Suzuki reaction by working in an aqueous medium, namely by condensation between phenyl derivatives substituted by a leaving group and benzeneboronic acids in the presence of a catalyst, strong base(s) and phase transfer agent according to the conditions described by D. Badone et al., 212th ACS National Meeting, American Chemical Society, Orlando Fla., Aug. 25–29, 1996, Abstract 351).

The activity of the compounds of formula (I), in particular that of the compounds (I'), on the nervous system was demonstrated in in vitro and in vivo studies according to the methods described in EP-0 458 696 and neuronal survival was evaluated with the aid of an in vitro survival test performed by using isolated neurons from dissections of the septal region of rat embryos.

More particularly, a sample of the septal region of 17–18 days old rats was taken under a dissection microscope under sterile conditions, then it was dissociated in trypsin-EDTA medium. The cell suspension was placed in a culture flask in DME/Ham's F12 medium (v:v) (Dulbecco Modified Eagle medium/Ham's F12 Nutrient mixture—R. G. Ham, Proc. Nat. Sci., 1965, 53: 288) containing 5% calf serum and 5% horse serum and maintained at 37° C. for 90 minutes. This treatment permits the elimination of non-neuronal cells.

The neuroblasts are then inoculated into the wells of a titration plate at $17 \times 10^4$ cells/cm$^2$ in a non-serum culture medium constituted by DME/Ham's F12 containing selenium (30 nM) and transferrin (1.25 mM). Each well was subject to prior treatment with poly-L-lysine. The inoculated plates are placed in an incubator (37° C.; 5% CO2).

The test compounds are dissolved in DMSO and diluted as required by the culture medium.

The neuroblasts are maintained on plates containing the test compound or the corresponding solvent for 4 days without changing the medium.

After 4 days the medium is replaced by culture medium in which a tetrazolium salt is dissolved (0.15 mg/ml). The cells are then placed in the incubator at 37° C. for 4 hours. The mitochondrial succinate dehydrogenases of the living cells reduce the tetrazolium salt to formazan blue, the optical density of which is measured at 540 nm after dissolution in DMSO and which is linearly correlated with the number of living cells (Manthorpe et al., Dev. Brain Res., 1988, 25: 191–198).

The difference between the groups containing the test compounds and the controls was evaluated by statistical analysis using the two-tailed Dunnett t-test.

In this latter test the compounds of formula (I), in particular those of formula (I'), proved to be as active or more active than the compounds described in EP-0 458 696, the efficacy of certain compounds of formula (I') on the neuronal survival being twice that of compound A described in EP-0 458 696.

As a result of this potent neuroprotective activity and their low toxicity compatible with use as medicines, the compounds of formula (I), in particular those of formula (I'), as well as their pharmaceutically acceptable addition salts, their solvates and their quaternary ammonium salts, in particular those of formula (I"), may be used for the preparation of pharmaceutical compositions indicated in the treatment and/or prophylaxis of all diseases which involve neuronal degeneration, a use which constitutes a further feature of the present invention. More particularly, the invention relates to the use of the compounds of formula (I), in particular (I') and (I"), alone or on co-administration or combination with other active ingredients acting on the CNS, for example, acetylcholinesterase inhibitors, selective M1 cholinomimetics, NMDA antagonists, nootropics such as piracetam in the following indications: memory disorders, vascular dementia, post-encephalitic disorders, post-apoplectic disorders, post-traumatic syndromes due to a cranial traumatism, Alzheimer's disease, senile dementia, subcortical dementia, such as Huntington chorea and Parkinson's disease, dementia caused by AIDS, neuropathies resulting from morbidity or damage to sympathetic or sensory nerves, cerebral diseases such as cerebral oedema and spinocerebellar degenerations, degeneration of motoneurons like for example amyotrophic lateral sclerosis.

The administration of the compounds accordiing to the invention may be suitably performed by the oral, parenteral, sublingual or transdermal route. The quantity of active ingredient to be administered in the treatment of cerebral and neuronal disorders according to the method of the present invention depends on the nature and gravity of the diseases to be treated as well as on the weight of the patients. In general, the total dose in man varies between 1 and 1400 mg per day, advantageously between 2 and 900 mg per day, for example 3 to 500 mg, more suitably from 10 to 300 mg per day in pharmaceutical compositions. The compositions of the present invention are preferably administered in the form of dosage units. These unit doses will usually comprise from 0.5 to 700 mg, advantageously from 2 to 300 mg, preferably from 5 to 150 mg, for example between 5 and 50 mg, namely 1, 2, 5, 10, 15, 20, 25, 30, 40 or 50 mg of product. These unit doses will usually be administered once or several times a day, for example 2, 3, 4 or 5 times per day, preferably one to three times a day.

According to another of its features, the object of the present invention is a pharmaceutical composition containing as active ingredients a compound of formula (I) above and a compound indicated in the symptomatic treatment of senile dementia of the Alzheimer type (DAT) or their pharmaceutically acceptable salts.

The expression "compound indicated in the symptomatic treatment of senile dementia of the Alzheimer type (DAT)"

indicates a product which is capable of improving the symptomatology of the patients suffering from DAT without having any effect on the causes of the disease.

Such compounds are for example acetylcholinesterase inhibitors, $M_1$ muscarinic agonists, nicotinic agonists, NMDA receptor antagonists, nootropic agents.

Preferred acetylcholinesterase inhibitors are tacrine and donepezil.

Other acetylcholinesterase inhibitors which may be used are for example rivastigmine (SDZ-ENA-713), galanthamine, metrifonate, eptastigmine, velnacrine, physostigmine (Drugs, 1997, 53 (5): 752–768; The Merck Index 12 ed.).

Other acetylcholinesterase inhibitors are also 5,7-dihydro-3-{2-{1-(phenylmethyl)-4-piperidinyl}ethyl}-6H-pyrrolo {3,2-f}-1,2-benzisoxazol-6-one, also known as icopezil (J. Med. Chem., 1995, 38: 2802–2808), MDL-73,745 or zifrosilone (Eur. J. Pharmacol., 1995, 276: 93–99), TAK-147 (J. Med. Chem., 1994, 37: 2292–2299).

Other acetylcholinesterase inhibitors are for example those which are described in the patent applications JP 09-095483, WO 97/13754, WO 97/21681, WO 97/19929, ZA 96-04565, U.S. Pat. No. 5,455,245, WO 95-21822, EP 637 586, U.S. Pat. No. 5,401,749, EP 742 207, U.S. Pat. No. 5,547,960, WO 96/20176, WO 96/02524, EP 677 516, JP 07-188177, JP 07-133274, EP 649 846, EP 648 771, JP 07-048370, U.S. Pat. No. 5,391,553, WO 94/29272, EP 627 400.

According to another of its features, the present invention relates to a pharmaceutical composition containing as active ingredient a compound of formula (I) and an $M_1$ receptor agonist, or their pharmaceutically acceptable salts.

$M_1$ receptor agonists are, for example, milameline, besipiridine, talsaclidine, xanomeline, YM-796 and YM-954 (Eur. J. Pharmacol., 1990, 187: 479–486), 3-{N-(2-diethylamino-2-methylpropyl)-6-phenyl-5-propyl}-pyridazinamine, also known as SR-46559 (Biorg. Med. Chem. Let., 1992, 2: 833–838), AF-102, CI-979, L-689,660, LU 25-109, S-99 77-2, SB 202,026, thiopilocarpine, WAL 2014 (Pharmacol. Toxicol., 1996, 78: 59–68).

According to another feature, the invention relates to a pharmaceutical composition containing as active ingredient a compound of formula (I) and a nicotinic agonist or their pharmaceutically acceptable salts.

Advantageous nicotinic agonists are for example MKC-231 (Biorg. Med. Chem. Let., 1995, 5 (14): 1495–1500), T-588 (Japan J. Pharmacol., 1993, 62: 81–86), ABT-418 (Br. J. Pharmacol., 1997, 120: 429–438).

According to another feature, the invention relates to a pharmaceutical composition containing as active ingredient a compound of formula (I) and an N-methyl-D-aspartate (NMDA) receptor antagonist or their pharmaceutically acceptable salts.

A particularly advantageous NMDA receptor antagonist is, for example, memantine (Arzneim. Forsch., 1991, 41, 773–780).

According to another feature, the invention relates to a pharmaceutical composition containing as active ingredient a compound of formula (I) and a nootropic agent or their pharmaceutically acceptable salts.

Nootropic agents which may be used according to the invention are, for example, netiracetam and nebracetam (Merck Index, 12th ed.).

The doses of the two combined active ingredients are usually selected from the doses of each medicine which would be administered in an uncombined treatment.

In accordance with another feature, the present invention also relates to a method for the treatment of senile dementia of the Alzheimer type which consists of the administration to a patient suffering from this disease of an efficacious dose of a compound of formula (I) or of one of its pharmaceutically acceptable salts and of an efficacious dose of a compound indicated in the symptomatic treatment of DAT or of one of its pharmaceutically acceptable salts, said administrations being simultaneous, sequential or alternating at intervals and the efficacious doses of the active ingredients being contained in separate unit forms of administration or, when the active ingredients are administered simultaneously, the two active ingredients being advantageously contained in a single pharmaceutical form.

Thus, the present invention relates, in accordance with another of its features, to pharmaceutical compositions containing as active ingredient a compound of formula (I') or one of its pharmaceutically acceptable salts or solvates or one of its quaternary ammonium salts, in particular of formula (I").

In the pharmaceutical compositions of the present invention for oral, sublingual, subcutaneous, intramuscular, intravenous, transdermal or rectal administration, the active ingredient may be administered in a unit form of administration, either as such for example, in lyophilized form or in a mixture with standard pharmaceutical vehicles, to animals and to human beings for the treatment of the above-mentioned diseases. The appropriate unit forms of administration include the oral forms such as optionally divisible tablets, capsules, powders, granules and oral solutions or suspensions, the forms for sublingual and buccal administration, the forms for subcutaneous, intramuscular or intravenous administration, the forms for topical administration and the forms for rectal administration.

When a solid composition is prepared in the form of tablets, the principal active ingredient is mixed with a pharmaceutical vehicle such as gelatin, starch, lactose, magnesium stearate, talc, gum arabic or the like. The tablets may be coated with sucrose or other suitable materials or they may also be treated so that they have a prolonged or delayed activity and so that they continuously release a predefined quantity of active ingredient.

A preparation of capsules is obtained by mixing the active ingredient with a diluent and by pouring the mixture obtained into soft or hard capsules.

A preparation in the form of a syrup or elixir may contain the active ingredient together with a sweetening agent, preferably calorie-free, methylparaben and propylparaben as antiseptics, as well as a flavouring agent and a suitable colouring matter.

The powders and granules dispersible in water may contain the active ingredient in a mixture with dispersion agents or wetting agents, or suspension agents like polyvinylpyrrolidone, and also with sweetening agents or flavour correctors.

For rectal administration, recourse is had to suppositories which are prepared with binders melting at the rectal temperature, for example, for example cocoa butter or polyethyleneglycols.

For parenteral administration, aqueous suspensions, saline solutions or sterile and injectable solutions which contain pharmacologically compatible dispersion and/or wetting agents, for example propyleneglycol or butyleneglycol, are used.

The active ingredient may also be formulated in the form of microcapsules, optionally with one or more vehicles or additives.

In the pharmaceutical compositions according to the present invention, the active ingredient may also be in the form of an inclusion complex in cyclodextrins, their ethers or their esters.

The examples which follow provide a better illustration of the invention.

EXAMPLE 1

1-{2-(3'-chlorobiphenyl-4-yl)-2-oxoethyl}-4-(3-trifluoromethylphenyl)-1,2,3,6-tetrahydropyridine hydrochloride 1a/ 1-bromo-2-(3'-chlorobiphenyl-4-yl)ethanone A mixture of 5 g (0.026 mole) of 3-chlorobiphenyl, 50 ml of methylene chloride, 6.95 g (0.034 mole) of bromoacetyl bromide is cooled to 0–5° C. and 4 g (0.030 mole) of aluminium trichloride are added. The mixture is stirred for 1 hour at 5° C., then for 4 hours at room temperature. It is poured onto an ice/water mixture, extracted with methylene chloride, the organic phase is washed with a 1N solution of HCl, dried over sodium sulfate and evaporated under reduced pressure. 4.5 g of the title product is obtained. M.p. 63–65° C.

1b/ 1-{2-(3'-chlorobiphenyl-4-yl)-2-oxoethyl}-4-(3-trifluoromethylphenyl)-1,2,3,6-tetrahydropyridine hydrochloride.

A mixture of 0.4 g (0.013 mole) of the product from the previous step, 2.95 g (0.013 mole) of 4-(3-trifluoromethyl-phenyl)-1,2,3,6-tetrahydropyridine, 80 ml of ethanol and 2.32 g (0.0167 mole) of powdered anhydrous potassium carbonate is heated at reflux for 1 hour. The salts are removed by filtration and the solution is acidified by addition of a hydrochloric acid-saturated ethanol solution. It is concentrated to about 40 ml under reduced pressure and left to stand overnight at 5° C. The precipitate is filter off, washed with water and then with isopropanol. 4.9 g of the title compound are obtained. M.p. 217–220° C.

EXAMPLE 2

1-{2-(2'-chlorobiphenyl-4-yl)-2-oxoethyl}-4-(3-trifluoromethylphenyl)-1,2,3,6-tetrahydropyridine hydrochloride On working as described in Example 1 but by using 2-chloro-biphenyl instead of 3-chlorobiphenyl, the title compound is obtained. M.p. 200–202° C. (crystallized from isopropanol).

EXAMPLE 3

1-{2-(4'-chlorobiphenyl-4-yl)-2-oxoethyl}-4-(3-trifluoromethylphenyl)-1,2,3,6-tetrahydropyridine hydrochloride On working as described in Example 1 but by using 4-chloro-biphenyl instead of 3-chlorobiphenyl, the title compound is obtained. M.p. 210–215° C.

EXAMPLE 4

1-{2-(4-isobutylphenyl)-2-oxoethyl}-4-(3-trifluoromethylphenyl)-1,2,3,6-tetrahydropyridine hydrochloride On working as described in Example 1 but by using 4-isobutyl-benzene instead of 3-chlorobiphenyl, the title compound is obtained. M.p. 224–228° C. (crystallized from isopropanol).

EXAMPLE 5

1-{2-(4-phenoxyphenyl)-2-oxoethyl}-4-(3-trifluoromethylphenyl)-1,2,3,6-tetrahydropyridine hydrochloride On working as described in Example 1 but by using diphenyl-ether instead of 3-chlorobiphenyl, the title compound is obtained. M.p. 205–210° C.

EXAMPLE 6

1-{2-(4-cyclohexylphenyl)-2-oxoethyl}-4-(3-trifluoromethylphenyl)-1,2,3,6-tetrahydropyridine hydrochloride On working as described in Example 1 but by using cyclo-hexylbenzene instead of 3-chlorobiphenyl, the title compound is obtained. M.p. 209–213° C. (crystallized from isopropanol).

EXAMPLE 7

1-{2-(4'-fluorobiphenyl-4-yl)-2-oxoethyl}-4-(3-trifluoromethyl-phenyl)-1,2,3,6-tetrahydropyridine hydrochloride On working as described in Example 1 but by using 4-fluoro-biphenyl instead of 3-chlorobiphenyl, the title compound is obtained. M.p. 123–125° C. (crystallized from isopropanol).

EXAMPLE 8

1-{2-(biphenyl-4-yl)-2-oxoethyl}-4-(3-trifluoromethylphenyl)-1,2,3,6-tetrahydropyridine hydrochloride On working as described in Example 1 but by using biphenyl instead of 3-chlorobiphenyl, the title compound is obtained. M.p. 145–147° C. (base); m.p. 240–243° C. (hydrochloride).

EXAMPLE 9

1-{2-(4-n-butylphenyl)-2-oxoethyl}-4-(3-trifluoromethylphenyl)-1,2,3,6-tetrahydropyridine hydrochloride On working as described in Example 1 but by using 4-n-butyl-benzene instead of 3-chlorobiphenyl, the title compound is obtained. M.p. 218–221° C.

EXAMPLE 10

1-{2-(4-t-butylphenyl)-2-oxoethyl}-4-(3-trifluoromethylphenyl)-1,2,3,6-tetrahydropyridine hydrochloride On working as described in Example 1 but by using 4-t-butyl-benzene instead of 3-chlorobiphenyl, the title compound is obtained. M.p. 97–9° C. (base).

EXAMPLE 11

1-{2-(3,4-diethylphenyl)-2-oxoethyl}-4-(3-trifluoromethylphenyl)-1,2,3,6-tetrahydropyridine hydrochloride On working as described in Example 1 but by using 3,4-diethylbenzene instead of 3-chlorobiphenyl, the title compound is obtained. M.p. 232–234° C.

EXAMPLE 12

1-{2-(2'-trifluoromethylbiphenyl-4-yl)-2-oxoethyl}-4-(3-trifluoromethylphenyl)-1,2,3,6-tetrahydropyridine hydrochloride 12a/ 2-(4-bromophenyl)-2,2-dimethoxyethane A mixture of 2 g (0.01 mole) of 4-bromoacetophenone, 5.6 ml of trimethyl orthoformate, 5.6 ml of methanol and 0.67 g of Amberlite® IR 120 is heated at reflux for 3 hours. After cooling, the mixture is filtered through Celite® and the filtered solution is evaporated. 2.4 g of the title compound are obtained in the form of an oil.

12b/ 2,2-dimethoxy-2-(2'-trifluoromethylbiphenyl-4-yl) ethane

A mixture of 4.9 g (14 mmole) of the product from the previous step, 2.45 g (16 mmole) of 2-trifluoromethylbenzene-boronic acid, 63 mg (0.28 mmole) of palladium acetate, 4.84 g (35 mmole) of potassium carbonate and 4.5 g (14 mmole) of
tetrabutylammonium bromide in 19 ml of water is stirred at 70° C. for 1 hour. It is allowed to cool and extracted with ethyl acetate. The organic phase is dried over sodium sulfate, filtered and the solvent is evaporated under reduced pressure. The title compound is obtained in the form of an oil.

12c/ 4-(2-trifluorophenyl)acetophenone

A solution of 4 ml of trifluoroacetic acid and 4 ml of water is added at 0° C. to a solution of 4.6 g (0.0105 mole) of the product from the previous step in 4 ml of methylene chloride. The mixture is stirred at room temperature for 2 hours, poured into water and extracted with methylene chloride. The organic phase is dried, filtered and the solvent is evaporated under reduced pressure. The crude product is purified by chromatograpphy on a silica gel column by elution with a cyclohexane/ethyl acetate mixture=9/1. 1.97 g of the title compound are obtained.

12d/ a-bromo-4-(2-trifluoromethylphenyl)acetophenone

To a solution of 1.97 g (7.5 mmole) of the product from the previous step in 5.4 ml of methanol, 0.38 ml (7.5 mmole) of bromine is added dropwise at 0° C. The mixture is stirred at room temperature for 3 hours, the solvent is evaporated, the residue is taken up in water and the solution is extracted with ethyl acetate. The organic phase is dried over sodium sulfate, filtered and the solvent is evaporated under reduced pressure. The title compound is obtained.

12e/ 1-{2-(2'-trifluoromethylbiphenyl-4-yl)-2-oxoethyl}-4-(3-trifluoromethylphenyl)-1,2,3,6-tetrahydropyridine hydrochloride.

A mixture of 0.74 g (0.0028 mole) of 4-(3-trifluoromethyl-phenyl)-1,2,3,6-tetrahydropyridine, 14 ml of ethanol and 1.27 g (0.0092 mole) of powdered anhydrous potassium carbonate is heated at reflux for 1 hour. A solution of 1.2 g (0.0035 mole) of the oil from the previous step in 3 ml of ethanol is added and refluxed for 30 minutes. The salts are removed by filtration and the solution is acidified by addition of a 1N aqueous solution of hydrochloric acid. The solvent is evaporated under reduced pressure, the residue is extracted with chloroform, the organic phase is dried over sodium sulfate, filtered and the solvent is evaporated under reduced pressure. The free base is obtained with the aid of a concentrated solution of ammonia and extracted with ethyl acetate and the product is purified by chromatography on a silica gel column by elution with a cyclohexane/ethyl acetate mixture=8/2. The title compound is obtained. The hydrochloride is prepared with the aid of an isopropanol solution saturated with hydrochloric acid. M.p. 195–197° C.

EXAMPLE 13

1-{2-(3'-trifluoromethylbiphenyl-4-yl)-2-oxoethyl}-4-(3-trifluoromethylphenyl)-1,2,3,6-tetrahydropyridine hydrochloride On working as described in Example 12 but by using 3-trifluoromethylbenzeneboronic acid instead of 2-trifluoromethylbenzeneboronic acid in step 12b/, the title compound is obtained. M.p. 232–234° C.

EXAMPLE 14

1-{2-(4'-trifluoromethylbiphenyl-4-yl)-2-oxoethyl}-4-(3-trifluoromethylphenyl)-1,2,3,6-tetrahydropyridine hydrochloride On working as described in Example 12 but by using 4-trifluoromethylbenzeneboronic acid instead of 2-trifluoromethylbenzeneboronic acid in step 12b/, the title compound is obtained. M.p. 245–247° C.

What is claimed is:

1. A compound of formula (I')

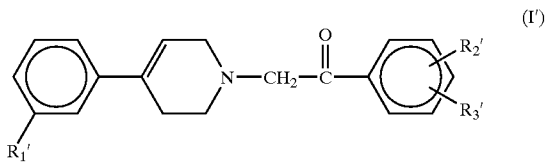

in which

R'$_1$ is halogen, a CF$_3$, (C$_1$–C$_4$) alkyl or (C$_1$–C$_4$) alkoxy group;

R'$_2$ is phenyl, phenoxy, phenylmethyl or phenylethyl, said groups optionally mono- or polysubstituted on the phenyl group by halogen, CF$_3$, (C$_1$–C$_4$) alkyl or (C$_1$–C$_4$) alkoxy;

R'$_3$ is hydrogen, (C$_1$–C$_6$) alkyl, (C$_1$–C$_6$) alkoxy, halogen, a CF$_3$ group or hydroxy;

or a salt or quaternary ammonium salt thereof.

2. A compound according to claim 1 selected from the group consisting of:

1-{2-(3'-chlorobiphenyl-4-yl)-2-oxoethyl}-4-(3-trifluoromethyl-phenyl)-1,2,3,6-tetrahydropyridine;

1-{2-(2'-chlorobiphenyl-4-yl)-2-oxoethyl}-4-(3-trifluoromethyl-phenyl)-1,2,3,6-tetrahydropyridine;

1-{2-(4'-chlorobiphenyl-4-yl)-2-oxoethyl}-4-(3-trifluoromethyl-phenyl)-1,2,3,6-tetrahydropyridine;

1-{2-(4-benzylphenyl)-2-oxoethyl}-4-(3-trifluoromethyl-phenyl)-1,2,3,6-tetrahydropyridine;

1-{2-(4'-fluorobiphenyl-4-yl)-2-oxoethyl}-4-(3-trifluoromethyl-phenyl)-1,2,3,6-tetrahydropyridine;

1-{2-(biphenyl-4-yl)-2-oxoethyl}-4-(3-trifluoromethyl-phenyl)-1,2,3,6-tetrahydropyridine;

1-{2-(2'-trifluoromethylbiphenyl-4-yl)-2-oxoethyl}-4-(3-trifluoromethyl-phenyl)-1,2,3,6-tetrahydropyridine;

1-{2-(3'-trifluoromethylbiphenyl-4-yl)-2-oxoethyl}-4-(3-trifluoromethyl-phenyl)-1,2,3,6-tetrahydropyridine;

1-{2-(4'-trifluoromethylbiphenyl-4-yl)-2-oxoethyl}-4-(3-trifluoromethyl-phenyl)-1,2,3,6-tetrahydropyridine;

or a pharmaceutically acceptable salt thereof.

3. A pharmaceutical composition comprising a compound according to claim 1 together with a pharmaceutically acceptable vehicle or diluent.

4. A pharmaceutical composition comprising a compound according to claim 2 together with a pharmaceutically acceptable vehicle or diluent.

* * * * *